United States Patent [19]  
Kay

[11] 4,113,757  
[45] Sep. 12, 1978

[54] TITANIUM COMPOUNDS
[75] Inventor: Peter Dunlop Kay, Hartlepool, England
[73] Assignee: Tioxide Group Limited, Billingham, England
[21] Appl. No.: 774,140
[22] Filed: Mar. 3, 1977
[30] Foreign Application Priority Data
Mar. 13, 1976 [GB] United Kingdom ............... 10157/76
[51] Int. Cl.$^2$ ............................................. C07F 7/28
[52] U.S. Cl. ............................... 260/429.5; 260/429 J
[58] Field of Search ..................................... 260/429.5
[56] References Cited
U.S. PATENT DOCUMENTS

| | | | |
|---|---|---|---|
| 2,643,262 | 6/1953 | Bostwick | 260/429.5 |
| 2,809,162 | 10/1957 | Lowe | 260/429.5 X |
| 2,898,356 | 8/1959 | Russell | 260/429.5 |
| 2,913,469 | 11/1959 | Russell | 260/429.5 |
| 3,032,570 | 5/1962 | Haslam | 260/429.5 |
| 3,337,391 | 8/1967 | Clayton et al. | 260/429.5 X |
| 3,856,839 | 12/1974 | Smith et al. | 260/429.5 |

OTHER PUBLICATIONS

Yamamoto et al., J.A.C.S., 81,2663-7 (1959).  
Chemical Abstracts 51,12961b (1957).

Primary Examiner—Helen M. S. Sneed  
Attorney, Agent, or Firm—Schuyler, Birch, Swindler, McKie and Beckett

[57] ABSTRACT

A titanium chelate being the reaction product of ethylene glycol titanate, propylene glycol titanate, diethylene glycol titanate or hexylene glycol titanate and lactic acid, alpha-hydroxy-butyric acid, citric acid or glyceric acid. The chelates are particularly useful for gelling hydroxyl polymers such as polyvinyl alcohol in the form of solutions.

3 Claims, No Drawings

TITANIUM COMPOUNDS

This invention relates to titanium compounds and particularly to titanium chelates.

According to the present invention a titanium chelate comprises a reaction product of an alpha-hydroxy acid (as hereinafter defined) and ethylene glycol titanate, propylene glycol titanate, diethylene glycol titanate or hexylene glycol titanate.

According to the invention also a process for the manufacture of titanium chelates comprises reacting an alpha-hydroxy acid (as hereinafter defined) with ethylene glycol titanate, propylene glycol titanate, diethylene glycol titanate or hexylene glycol titanate.

By the term "alpha-hydroxy acid" as used in this specification there is meant lactic acid, alpha-hydroxybutyric acid, citric acid and glyceric acid.

It has been found that the titanium chelates of the present invention are eminently suitable for the gelling of hydroxyl polymers, e.g. polyvinyl alcohol, and its partial esters and acetals, cellulose derivatives and polymeric carbohydrates in weakly acidic, weakly basic and neutral solutions. The titanium chelates of the present invention are liquids and as such can be easily added to aqueous solutions of the hydroxyl polymers and furthermore during the preparation of the titanium chelates filtering of a liquid is not required to remove solid material.

The titanium chelates of the present invention are manufactured by a method which involves bringing together ethylene glycol titanate, propylene glycol titanate, diethylene glycol titanate or hexylene glycol titanate, and the alpha-hydroxy acid in any order. If desired, the alkylene glycol titanate can be pre-formed by mixing the appropriate glycol with a tetra-alkyl titanate, or if desired, the titanium chelate of the invention can be prepared by forming a mixture of a tetra-alkyl titanate, the appropriate glycol and the alpha-hydroxy acid. If desired, two or more of the glycol titanates can be employed, or as appropriate two or more of the glycols.

If desired, the alkylene glycol titanate can be pre-formed by reacting the glycol with titanium tetrachloride in the presence of ammonia and a solvent if desired.

Any tetra-alkyl titanate having the formula $Ti(OR)_4$ can be employed for the preparation of the particular glycol titanate, but preferably tetra-alkyl titanates are employed containing from 1 to 6 carbon atoms in the alkyl group and more particularly from 2 to 4 carbon atoms. When the titanium chelates are prepared employing a method in which a tetra-alkyl titanate, the appropriate glycol and the alpha-hydroxy acid are reacted in situ then it is preferred that the tetra-alkyl titanate should contain 1 to 3 carbon atoms in the alkyl group in order that the free alcohol liberated is readily soluble in aqueous media.

When the titanium chelates of the invention are prepared from pre-formed glycol titanates then these titanates may contain the particular free alcohol which is liberated during their manufacture from the tetra-alkyl titanate. However, if desired the free alcohol may be removed from the glycol titanate and this is particularly so when the alcohol which has been formed is not readily soluble in water. Preferably the particular glycol titanates are either pre-formed or formed in situ from tetraisopropyl titanate.

When the titanium chelates of the present invention are prepared by mixing a tetra-alkyl titanate with the appropriate glycol and the alpha-hydroxy acid then it is usual to employ from 1 to 4 moles of the glycol per mole of tetra-alkyl titanate and from 1 to 3, preferably 2, moles of the alpha-hydroxy acid. When the particular glycol titanate is pre-formed then it is usual to employ from 2 to 4 moles of the glycol per mole of tetra-alkyl titanate, usually 4 moles. Also when the chelate is prepared from pre-formed titanates then it is usual to employ from 1 to 3 moles, preferably 2 moles, of the alpha-hydroxy acid per mole of glycol titanate.

The particular titanium chelates of the invention when added to a hydroxyl polymer in aqueous solution gel the polymeric solution. Aqueous solutions of the hydroxylated polymers containing the gelling agent can be used as binding agents for glass fibres, clays, and as paper coatings, amongst other uses.

The invention is described in the following Examples:

EXAMPLE 1

424 grams (4M) diethylene glycol was added to 284 grams (1M) of tetraisopropyl titanate contained in a round-bottomed flask. 240 grams (4M) of isopropyl alcohol by weight was stripped from the product by vacuum distillation on a rotary evaporator. To the yellow viscous product so obtained were then added 180 grams (2M) of lactic acid to form the desired titanium chelate.

It was found that when 3 parts by weight of the titanium chelate obtained were mixed with 100 parts by weight of a 3% aqueous solution of polyvinyl alcohol that a thick gel was produced within 1 minute at 20° C.

EXAMPLE 2

1 mole of propylene glycol was added to 1 mole of isopropyl titanate followed by 2 moles of lactic acid. The product was a colourless viscous liquid readily soluble in water and produced a gel within 2 minutes when added to aqueous polyvinyl alcohol as described in Example 1.

EXAMPLE 3

The procedure of Example 2 was repeated except that 4 moles of propylene glycol was used. A similar product was obtained.

The chelate obtained was found to gel the aqueous polyvinyl alcohol in 1 minute at 30° C when used in amounts as described in Example 1.

EXAMPLE 4

The procedure of Example 3 was repeated but using 4 moles of ethylene glycol instead of propylene glycol.

The product gave a gel within 1 minute at 40° C when tested as described in Example 1.

EXAMPLE 5

3 moles of diethylene glycol were added to one mole of isopropyl titanate and 2 moles of lactic acid then added. The product was a colourless viscous liquid which gelled within 1 minute at 20° C when tested as described in Example 1.

EXAMPLE 6

2 moles of hexylene glycol were added to 1 mole of isopropyl titanate followed by 2 moles of lactic acid. The product was a colourless liquid. The chelate produced a gel within 2 minutes at 20° C when tested as described in Example 1.

What is claimed is:

1. A titanium chelate comprising a reaction product of an alpha-hydroxy acid selected from the class consisting of lactic acid, alpha-hydroxy butyric acid, citric acid and glyceric acid and a titanate selected from the class consisting of ethylene glycol titanate, propylene glycol titanate, diethylene glycol titanate and hexylene glycol titanate.

2. A titanium chelate according to claim 1 in which from 1 to 3 moles of said alpha-hydroxy acid are present per mole of said glycol titanate.

3. A titanium chelate according to claim 1 in which 2 moles of said alpha-hydroxy acid are present per mole of said particular glycol titanate.